United States Patent
Osa

(10) Patent No.: US 8,502,973 B2
(45) Date of Patent: Aug. 6, 2013

(54) OPTICAL EMISSION ANALYZER

(75) Inventor: Haruki Osa, Koka (JP)

(73) Assignee: Shimadzu Corporation, Kyoto (JP)

( * ) Notice: Subject to any disclaimer, the term of this patent is extended or adjusted under 35 U.S.C. 154(b) by 207 days.

(21) Appl. No.: 12/676,096

(22) PCT Filed: Sep. 4, 2007

(86) PCT No.: PCT/JP2007/000953
§ 371 (c)(1), (2), (4) Date: Mar. 2, 2010

(87) PCT Pub. No.: WO2009/031180
PCT Pub. Date: Mar. 12, 2009

(65) Prior Publication Data
US 2010/0208255 A1      Aug. 19, 2010

(51) Int. Cl.
*G01J 3/30* (2006.01)
(52) U.S. Cl.
USPC .......................................................... 356/313
(58) Field of Classification Search
USPC .......................................................... 356/313
See application file for complete search history.

(56) References Cited

U.S. PATENT DOCUMENTS
3,906,291 A * 9/1975 Schayes et al. .............. 315/171

FOREIGN PATENT DOCUMENTS
| JP | 2004-333323 A | 11/2004 |
| JP | 2005-069816 A | 3/2005 |
| JP | 2006-300630 A | 11/2006 |

* cited by examiner

*Primary Examiner* — Tara S Pajoohi Gomez
(74) *Attorney, Agent, or Firm* — Sughrue Mion, PLLC

(57) ABSTRACT

An optical emission analyzer is provided with a circuit-closing switch (56) for changing the state of an arc-generating circuit 5 between the closed state and the open state and a reverse-blocking diode (55) for preventing a spark current from flowing into the circuit-closing switch (56). The circuit-closing switch (56) is turned on before the beginning of a spark discharge between a discharge electrode (31) and a sample (32) to initiate excitation of a coil (53). Consequently, the excitation current of the coil (53) can be increased to a target value within the duration of the spark discharge without using a low-inductance coil or increasing the switching frequency of a switching element (52).

8 Claims, 7 Drawing Sheets

OPTICAL EMISSION ANALYZER

TECHNICAL FIELD

The present invention relates to an optical emission analyzer for analyzing the elementary composition of a sample by vaporizing constituent atoms of the sample by an electric discharge to cause an emission from those atoms, and measuring the intensity of the emission.

BACKGROUND ART

An optical emission analyzer is a device for determining the types of elements contained in a sample to be analyzed and the content of each element by exciting the sample into a light-emitting state, separating the emitted light a light-dispersing element or similar device into spectral lines characteristic of the constituent elements using, checking for the presence of each spectral line and, if the line is present, measuring its intensity. One method for causing an excitation emission of a sample to be analyzed is to generate a spark discharge within a space (or discharge gap) between the sample and a discharge electrode to simultaneously perform both the vaporization and excitation of the atoms on the sample surface by a discharge plasma (refer to Patent Document 1).

FIG. 5 is a circuit diagram showing the configuration of a conventional optical emission analyzer. This optical emission analyzer is composed of a capacitor circuit 1, igniter circuit 2, emission stand 3, photometric circuit 4 and arc-generating circuit 5. In the emission stand 3, a discharge electrode 31 and a sample 32 are provided. The igniter circuit 2, capacitor circuit 1 and arc-generating circuit 5 are connected in series to the discharge electrode 31 and the sample 32. The capacitor circuit 1 includes a capacitor-charging circuit 11, rectifying diode 12, capacitor 13 and clamp diode 14. The igniter circuit 2 has an igniter transformer 21 and igniter drive circuit 22.

The capacitor-charging circuit 11 charges the capacitor 13 to a predetermined voltage via the rectifying diode 12. After the charging of the capacitor 13 is completed, the igniter drive circuit 22 generates a high voltage in a secondary winding of the igniter transformer 21 to initiate an electric discharge between the discharge electrode 31 and the sample 32. Consequently, a spark current (discharge current) flows through the current path formed by the capacitor 13, igniter transformer 21, emission stand 3 and bypass diode 54, with the energy charged in the capacitor 13 being transferred into the space between the discharge electrode 31 and the sample 32 to create a plasma.

Meanwhile, in the arc-generating circuit 5, a switching element 52 is connected to a power source 51 simultaneously with the beginning of the spark discharge, to initiate excitation of a coil 53. The excitation current of the coil 53 increases when the switching element 52 is connected to the contact to the power source 51, and decreases when the switching element 52 is connected to the common contact. The switching action and frequency of the switching element 52 are controlled so as to maintain the excitation current of the coil 53 at a predetermined target value.

FIGS. 6 and 7 is a graph showing the relationship among the discharge current Id in the emission stand 3, the excitation current Ia in the coil 53 and the output voltage Va of the arc-generating circuit 5 in the case where the target value of the excitation current of the coil 53 is 10 A. After the spark discharge is initiated, the discharge current Id rapidly increases and then decreases with time. Meanwhile, the excitation current Ia gradually increases after the excitation of the coil 53 is initiated.

After the initiation of the spark discharge and excitation of the coil 53, the discharge current Id flows through both the coil 53 and bypass diode 54 during a period of time where the discharge current Id exceeds the excitation current Ia. When the discharge current Id becomes equal to the excitation current Ia, the bypass diode 54 turns off, after which only the excitation current Ia flows through the emission stand 3. As a result, the discharge between the discharge electrode 31 and the sample 32 changes to an arc discharge. The arc discharge between the discharge electrode 31 and the sample 32 is maintained while the switching element continues its switching action.

As shown in FIG. 6, if the excitation current Ia in the coil 53 reaches the target value within the duration of the spark discharge, a smooth transition is made from the spark discharge to the arc discharge. On the other hand, if, as shown in FIG. 7, the excitation current Ia in the coil 53 fails to reach the target value within the duration of the spark discharge, the waveform of the discharge current will be distorted (similar to the portion surrounded by broken line A in FIG. 7).

Patent Document 1: Japanese Unexamined Patent Application Publication No. 2006-300630

DISCLOSURE OF THE INVENTION

Problem to be Solved by the Invention

The duration of the spark discharge depends on the condition of the discharge electrode, the amount of inert gas (e.g. argon) between the discharge electrode and the sample, the amount of energy of the spark discharge and other factors, and hence cannot be arbitrarily controlled. The duration of the spark discharge is as short as several tens to hundreds of $\mu s$. To achieve a predetermined current value within such a short period of time, it is necessary to lower the inductance of the coil 53.

However, reducing the inductance of the coil 53 increases the ripple current of the excitation current, which deteriorates the accuracy and reproducibility of the analysis. Even if the inductance of the coil 53 is low, the ripple current will be suppressed and the excitation current of the coil 53 can rise quickly if the switching element 52 is operated at higher frequencies. However, raising the switching frequency increases the loss in the switching element 52, which causes a temperature rise inside the apparatus and accordingly deteriorates the accuracy and reproducibility of the analysis.

Thus, the problem to be solved by the present invention is to provide an optical emission analyzer with improved reproducibility of the discharge current and enhanced accuracy of the analysis.

Means for Solving the Problems

The present invention aimed at solving the previously described problem provides an optical emission analyzer including: an emission stand for generating an excitation emission between a sample and a discharge electrode; a capacitor circuit and an igniter circuit, for generating a spark discharge between the sample and the discharge electrode; and an arc-generating circuit including a power source, a coil and a switching element for exciting the coil by alternately connecting the coil to the power source and disconnecting the coil from the power source, with the igniter circuit, the capacitor circuit and the arc-generating circuit being connected in series to the emission stand to form a discharge path, and the optical emission analyzer is characterized by further including:

a switching means for changing the state of the arc-generating circuit between a closed state and an open state; and a control circuit for controlling the switching means to coordinate the timing of initiating the spark discharge and the timing of initiating the excitation of the coil so that the excitation current of the coil reaches a predetermined target value before the spark discharge ceases.

The switching means may preferably include a circuit-closing switch which is provided in parallel to the emission stand with respect to the arc-generating circuit and closes the arc-generating circuit when it is turned on, and a reverse-blocking diode for preventing a spark current from flowing into the circuit-closing switch. The control circuit may preferably turn on the circuit-closing switch before initiating the spark discharge between the sample and the discharge electrode and turns off the circuit-closing switch after the initiation of the spark discharge during a period of time where the spark current exceeds the excitation current of the coil.

Effect of the Invention

In the optical emission analyzer according to the present invention, the switching means for changing the state of the arc-generating circuit between the closed state and the open state enables the coil to be excited by changing the arc-discharging circuit to the closed state without supplying a discharge current to the emission stand. Accordingly, it is possible to initiate the excitation of the coil with arbitrary timing. This eliminates the necessity of using a low-inductance coil or increasing the switching frequency of the switching element to achieve a target value of the excitation current of the coil before the spark discharge ceases. Thus, the ripple current can be reduced. Furthermore, even if the amount of energy of the spark discharge is small and the duration of the spark discharge is accordingly short, the discharge current can be generated with high degrees of reproducibility, so that the analysis accuracy can be improved.

As long as the excitation current of the coil is increased to a target value before the spark discharge ceases, the excitation of the coil may be initiated at any point in time. Therefore, the excitation time of the coil will be shortened if the excitation of the coil is initiated at a point in time from which the excitation current of the coil can reach a predetermined target value within the duration of the spark discharge.

After the spark discharge has ceased, the capacitor in the capacitor circuit is charged by a capacitor-charging circuit. This capacitor-charging period can be utilized for the excitation of the coil when the period of time from the initiation of excitation of the coil to the initiation of the spark discharge is set at a length shorter than the period of time for the capacitor to be charged by the capacitor-charging circuit. Therefore, the analysis time does not become longer even when the initiation of excitation of the coil is advanced.

In the case where the switching means consists of a circuit-closing switch which closes the arc-generating circuit when it is turned on and a reverse-blocking diode for preventing a spark current from flowing into the circuit-closing switch, it is preferable to turn on the circuit-closing switch before the spark discharge is initiated and turn off the circuit-closing switch after the initiation of the spark discharge during a period of time where the spark current exceeds the excitation current of the coil, to generate an arc discharge. This switching operation ensures continuity of the excitation current flowing through the coil and thereby prevents counter electromotive forces from occurring in the coil.

EXPLANATION OF NUMERALS

1 . . . Capacitor Circuit
   11 . . . Capacitor-Charging Circuit
   12 . . . Rectifying Diode
   13 . . . Capacitor
   14 . . . Clamp Diode
2 . . . Igniter Circuit
   21 . . . Igniter Transformer
   22 . . . Igniter Drive Circuit
3 . . . Emission Stand
   31 . . . Discharge Electrode
   32 . . . Sample
4 . . . Photometric Circuit
5 . . . Arc-Generating Circuit
   51 . . . Power Source
   52 . . . Switching Element
   53 . . . Coil
   54 . . . Bypass Diode
   55 . . . Reverse-Blocking Diode
   56 . . . Circuit-Closing Switch
6 . . . Control Circuit

BEST MODE FOR CARRYING OUT THE INVENTION

Figure 1:
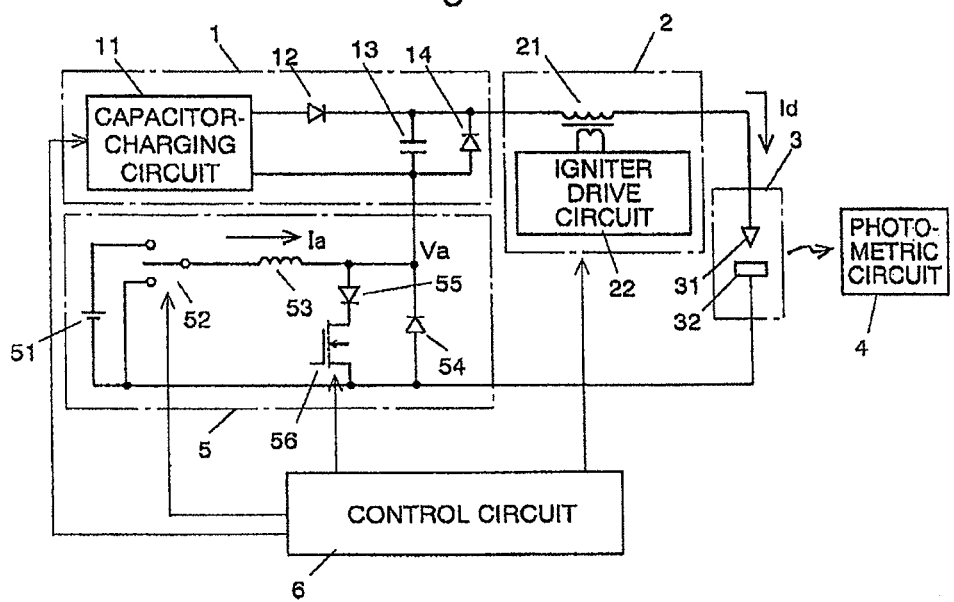
FIG. 1 is a block diagram showing the electrical configuration of an optical emission analyzer according to an embodiment of the present invention.

An embodiment of the optical emission analyzer according to the present invention is hereinafter described with reference to the attached drawings. FIG. 1 is a block diagram showing the electrical configuration of the optical emission analyzer according to the present embodiment. The components identical to those of the previously described conventional optical emission analyzer are denoted by the same numerals.

The optical emission analyzer according to the present embodiment includes a capacitor circuit 1, igniter circuit 2, emission stand 3, photometric circuit 4, arc-generating circuit 5 and control circuit 6 which controls the operations of these components. The capacitor circuit 1, igniter circuit 2, emission stand 3 and photometric circuit 4 are substantially identical to the corresponding components of the conventional optical emission analyzer. Therefore, no explanation will be made for them.

The optical emission analyzer of the present embodiment includes, as its characteristic components, a reverse-blocking diode and circuit-closing switch 56 which are provided in parallel to the emission stand with respect to the arc-generating circuit 5. The reverse-blocking diode 55, which is connected in series to the circuit-closing switch 56, prevents a spark current from flowing into the circuit-closing switch 56. The arc-generating circuit 5 is changed to the closed state when the circuit-closing switch 56 is turned on, and to the open state when the switch is turned off. The circuit-closing switch 56 and reverse-blocking diode 55 are connected parallel to the bypass diode 54.

Figure 2:
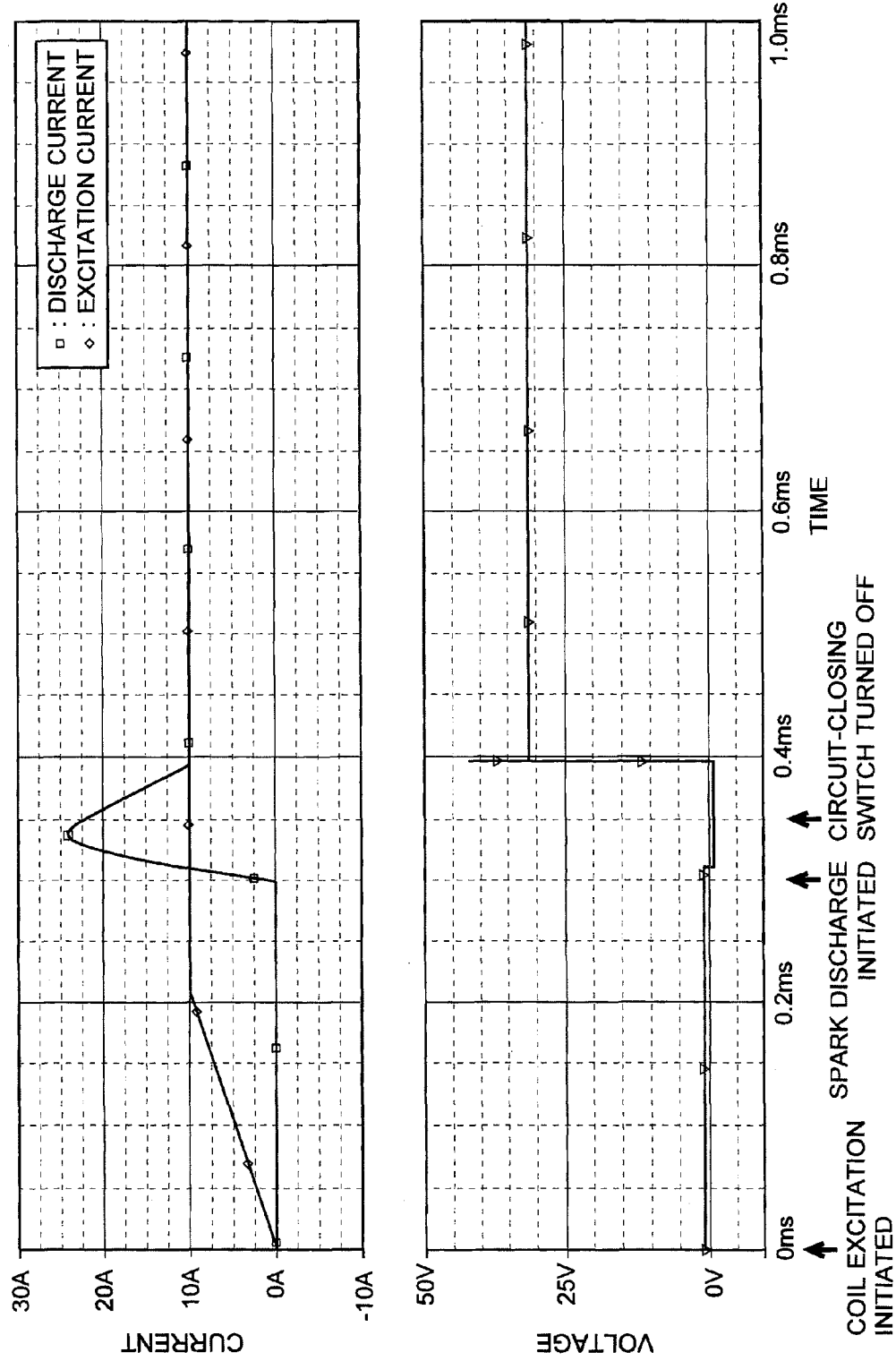
FIG. 2 is a graph showing an example of the discharge current, excitation current, and a waveform of the output voltage of an arc-generating circuit in the case where the circuit-closing switch 56 is turned off during a period of time where the spark current exceeds the excitation current.

An operation of the optical emission analyzer according to the present embodiment is hereinafter described with reference to FIG. 2. FIG. 2 shows an example of the discharge current Id flowing between the discharge electrode 31 and the sample 32, the excitation current Ia of the coil 53, and a waveform of the output voltage Va of the arc-generating circuit 5. The abscissa axis in FIG. 2 shows time (ms), and the coordinate axis shows either the current value (A) or voltage value (V).

The control circuit 6 initially turns on the circuit-closing switch 56 (at 0 ms) and simultaneously initiates the switching action of the switching element 52, whereby the excitation of the coil 53 is initiated. The excitation current Ia of the coil 53 increases when the switching element 52 is connected to the power source 51 and decreases when the switching element 52 is connected to a common point. The control circuit 6 regulates the operation of the switching element 52 so that the excitation current Ia of the coil 53 reaches the target value of 10 A. In the example shown in FIG. 2, the excitation current Ia reached the target value after 0.2 ms from the beginning of the excitation.

Subsequently the control circuit 6 energizes the igniter circuit 2 to give rise to a spark discharge between the discharge electrode 31 and the sample 32 (at 0.3 ms).

In the capacitor circuit 1, the capacitor-charging circuit 11 charges the capacitor 13 to a predetermined voltage via the rectifying diode 12. When the igniter drive circuit 22 generates a high voltage in the secondary winding of the igniter transformer 21, a spark current (or discharge current) Id flows through a discharge path that is formed by the capacitor 13, the secondary winding of the igniter transformer 21, the space between the discharge electrode 31 and the sample 32, and the bypass diode 54. Consequently, the energy charged in the capacitor 13 is transferred into the space between the discharge electrode 31 and the sample 32 to create a plasma.

After the spark discharge is initiated, the circuit-closing switch 56 in the arc-generating circuit 5 is turned off during a period of time where the spark discharge Id exceeds the excitation current Ia of the coil 53, e.g. after 0.05 ms from the initiation of the spark discharge (or 0.35 ms from the initiation of excitation). When the spark current Id exceeds the excitation current Ia, the spark current Id flows through both the bypass diode 54 and the coil 53, and no spark current Id flows through the circuit-closing switch 56. Therefore, even when the circuit-closing switch 56 is turned off, the continuity of the excitation current flowing through the coil 53 is maintained and no counter electromotive force occurs in the coil 53.

When the spark current Id decreasing with time becomes equal to the excitation current Ia in the coil 53, the bypass diode 54 turns off. As a result, only the excitation current Ia coming from the coil 53 flows through the space between the discharge electrode 31 and the sample 32. Thus, the transition to arc discharge occurs. This arc discharge is maintained while the switching element 52 continues its switching action.

Thus, in the present embodiment, the arc-generating circuit 5 is provided with the circuit-closing switch 56 so that the excitation of the coil 53 can be initiated even when no spark discharge is flowing through the emission stand 3. Therefore, it is possible to initiate the excitation of the coil 53 with arbitrary timing. Accordingly, it is unnecessary to use a low-inductance coil or increase the switching frequency of the switching element 52 to achieve a target value of the excitation current of the coil 53 within the duration of the spark discharge. Even if the amount of energy of the spark discharge is small and the duration of the spark discharge is accordingly short, it is possible to increase the excitation current of the coil 53 to a target value within the duration of the spark discharge by advancing the timing of initiating the excitation of the coil 53. Therefore, it is possible to improve the reproducibility of the discharge current and enhance the analysis accuracy.

Figure 3:
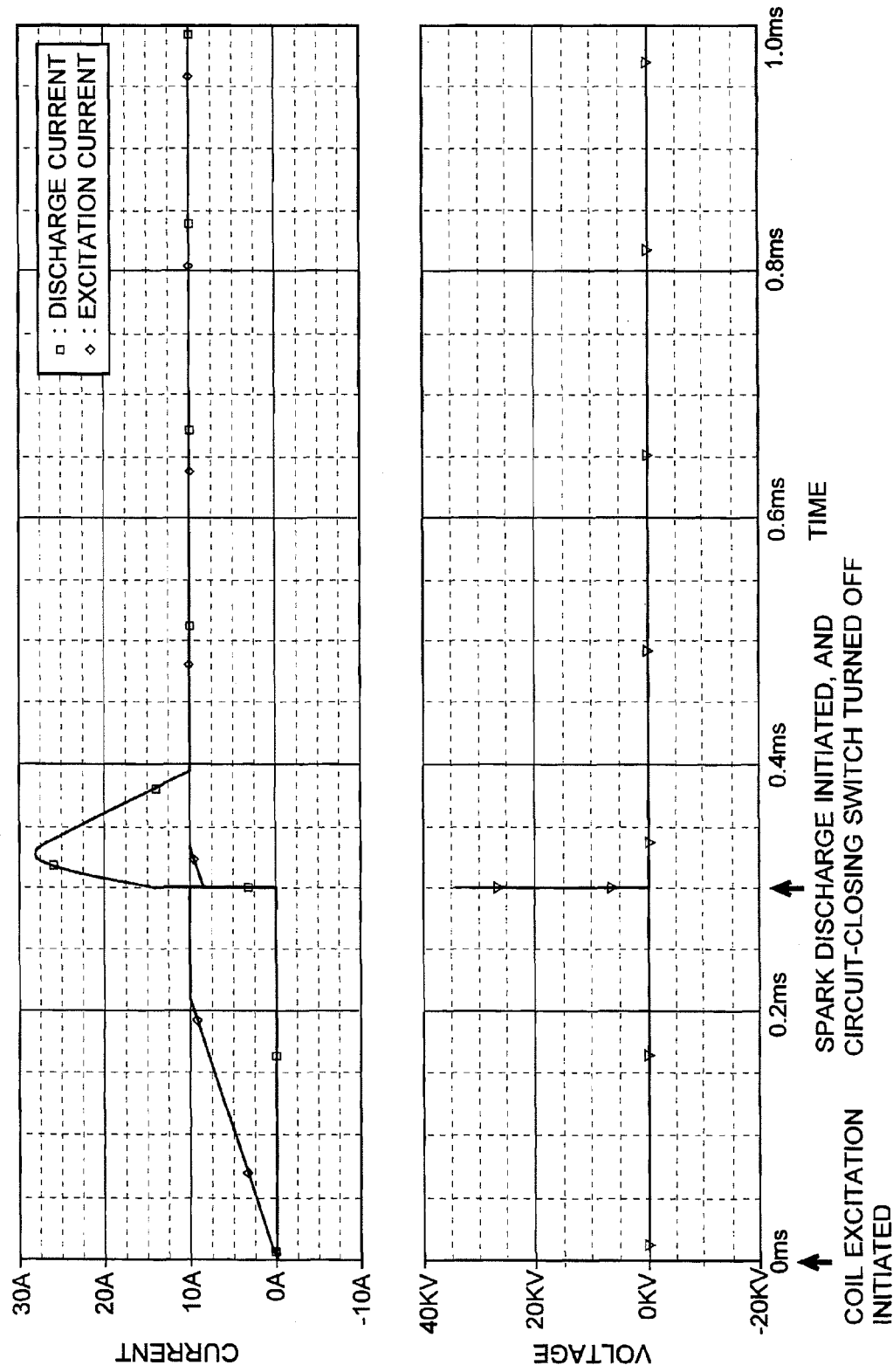
FIG. 3 is a graph showing an example of the discharge current, excitation current, and a waveform of the output voltage of an arc-generating circuit in the case where the circuit-closing switch is turned off while the spark current is below the excitation current.

In the present embodiment, the circuit-closing switch 56 is turned off during a period of time where the spark current exceeds the excitation current of the coil 53. This operation creates a reproducible waveform of the discharge current, so that the analysis accuracy can be further improved. For comparison, FIG. 3 shows the discharge current Id, excitation current Ia and a waveform of the output voltage Va of the arc-generating circuit in the case where the circuit-closing switch 56 is turned off simultaneously with the initiation of the spark discharge. Turning off the circuit-closing switch 56 at this point in time causes a discontinuous change in the excitation current of the coil 53 and generates a counter electromotive force in the coil 53. Consequently, a surge voltage occurs in the output of the arc-generating circuit 5.

Figure 4:
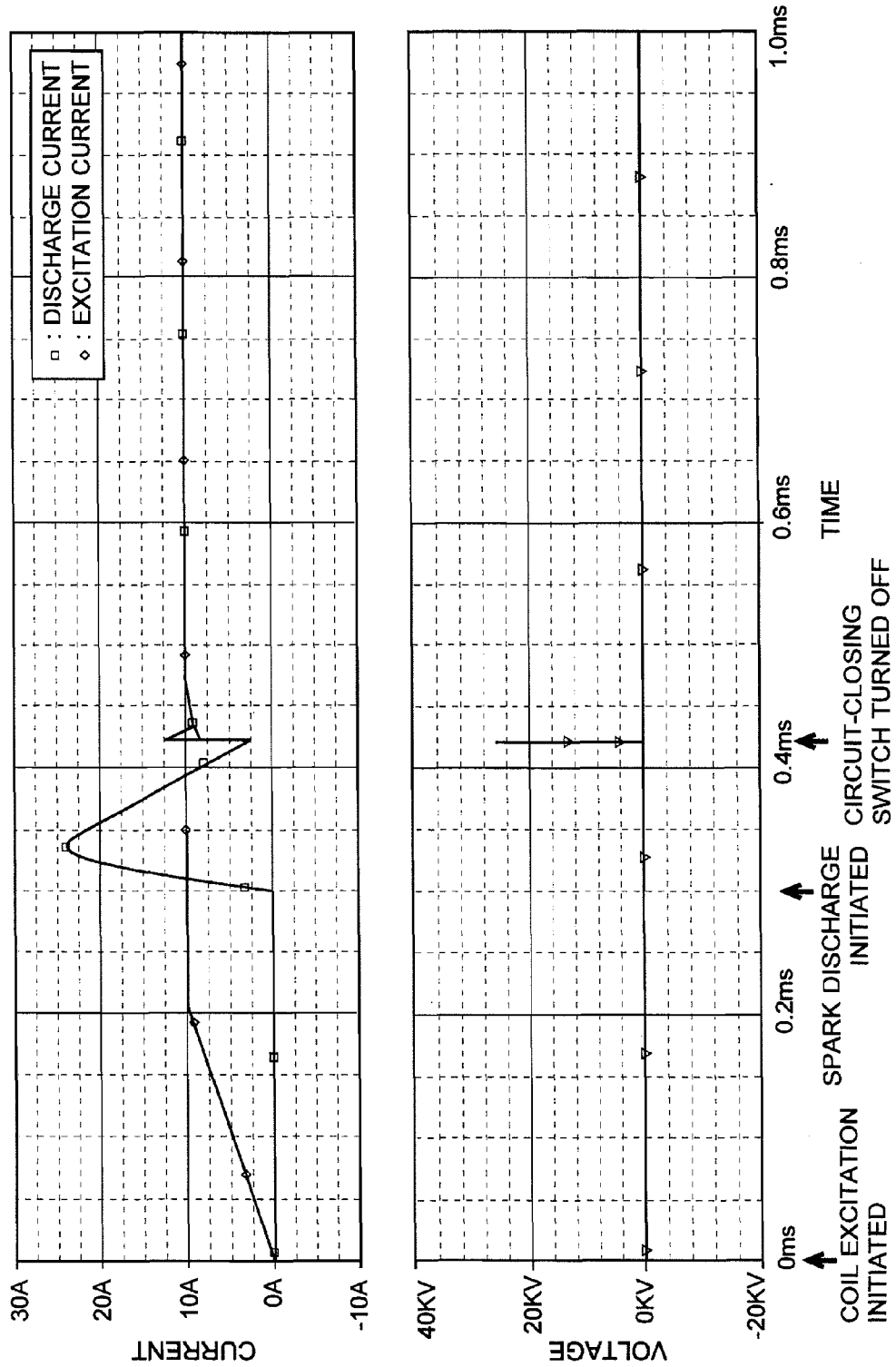
FIG. 4 is a graph showing another example of the discharge current, excitation current, and a waveform of the output voltage of an arc-generating circuit in the case where the circuit-closing switch is turned off while the spark current Id is below the excitation current.
Figure 5:
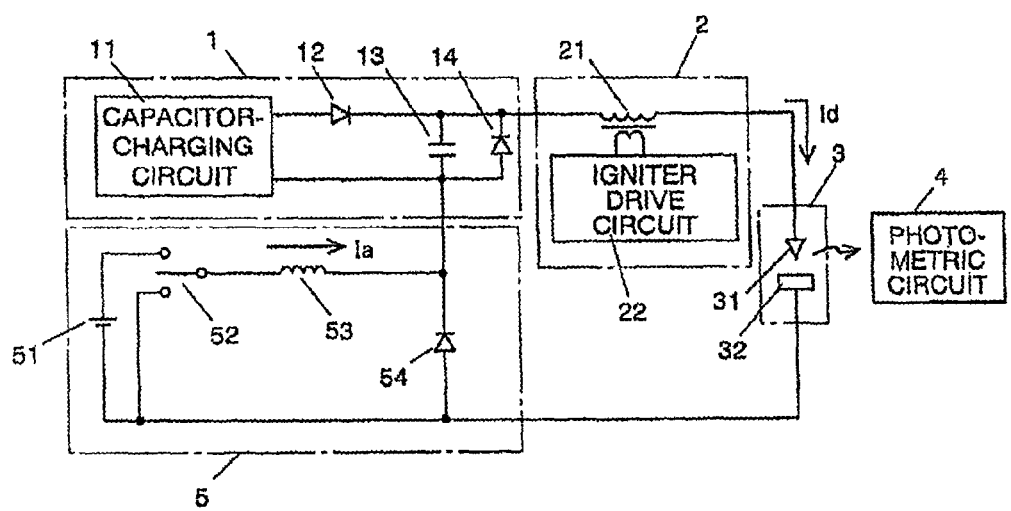
FIG. 5 is a block diagram showing the electrical configuration of a conventional optical emission analyzer.
Figure 6:
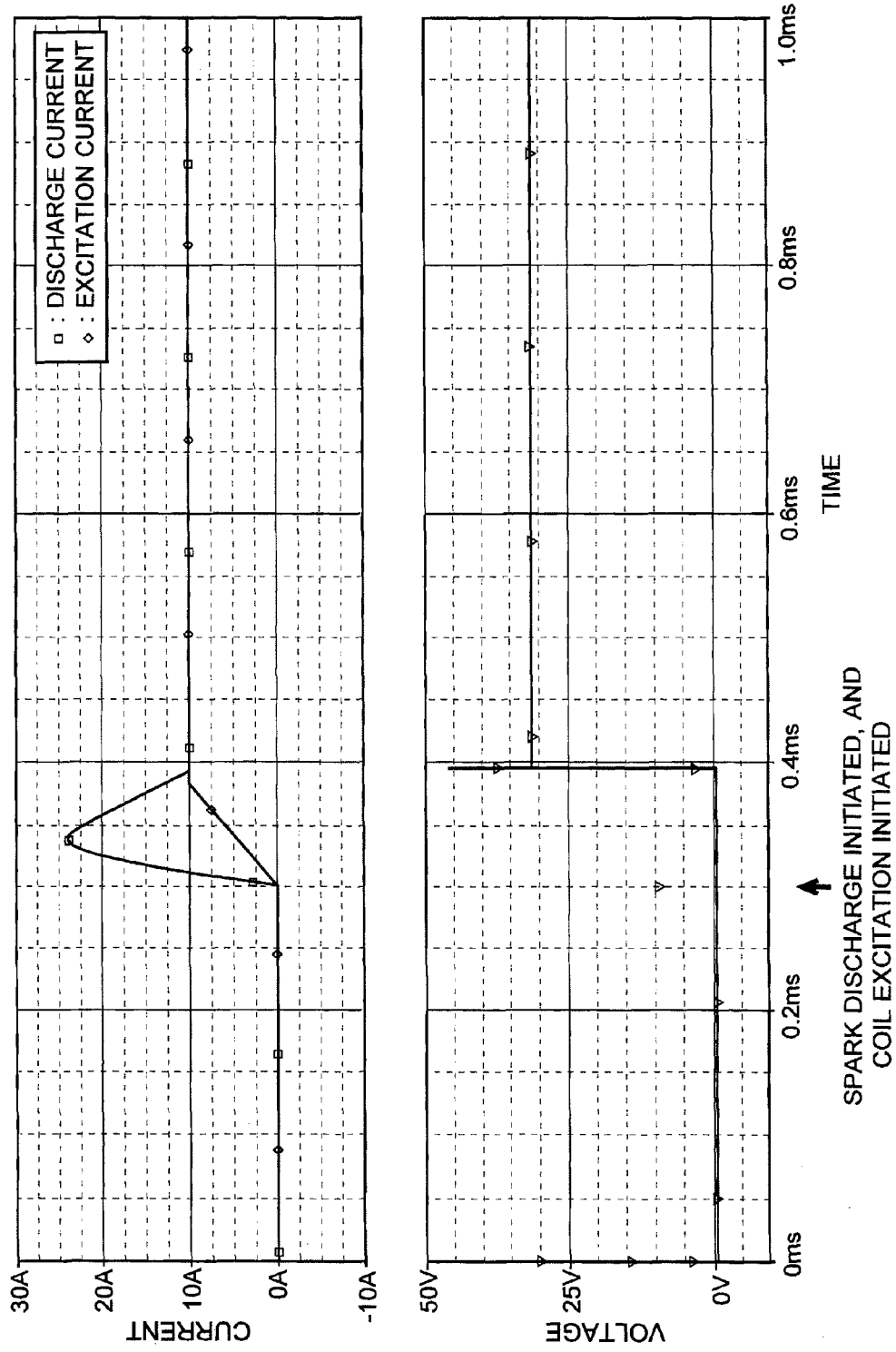
FIG. 6 a graph showing the discharge current, excitation current, and a waveform of the output voltage of an arc-generating circuit in the case where the excitation current of the coil reaches a target value within the duration of the spark current.
Figure 7:
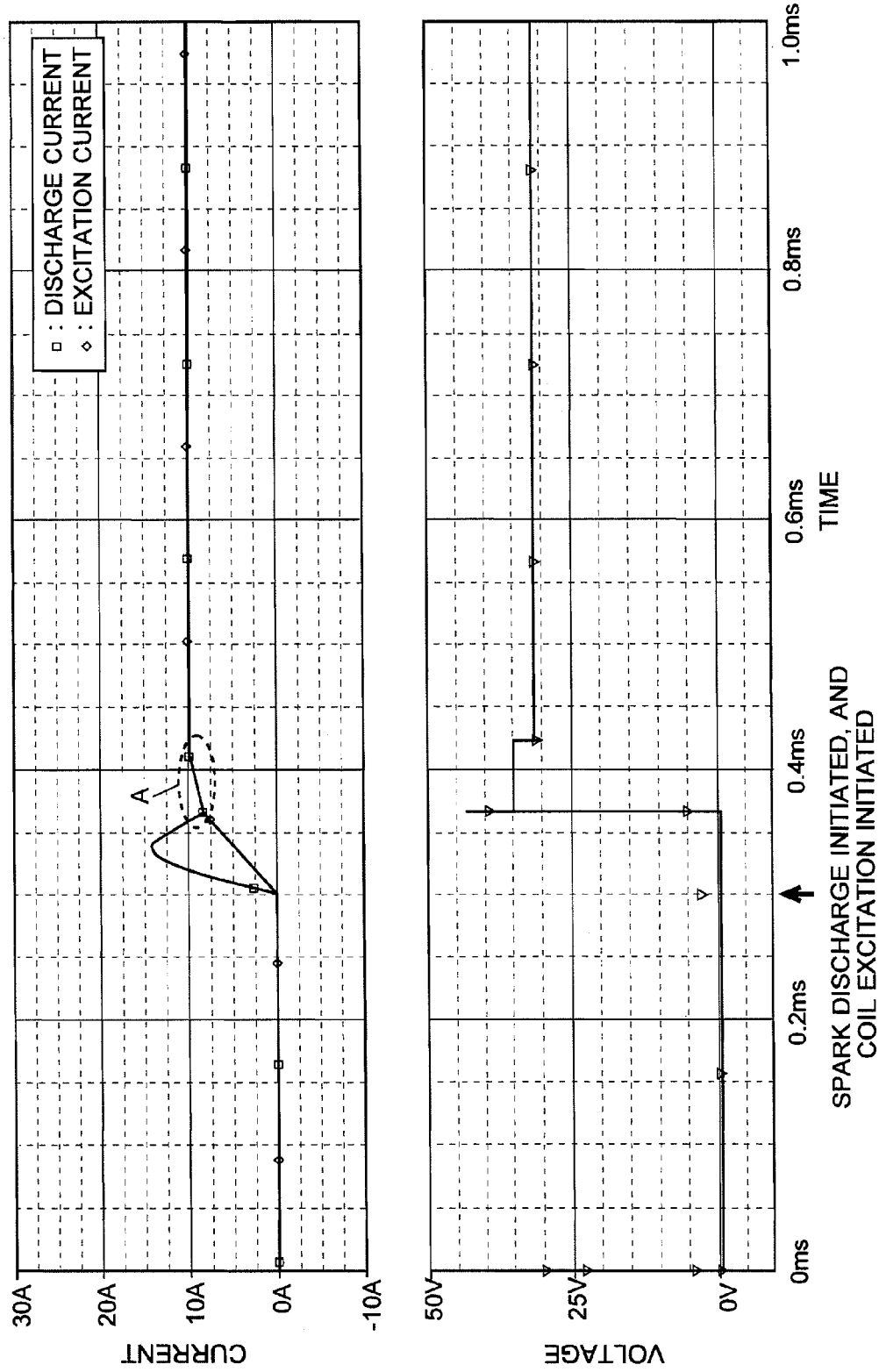
FIG. 7 a graph showing the discharge current, excitation current, and a waveform of the output voltage of an arc-generating circuit in the case where the excitation current of the coil does not reach a target value within the duration of the spark current.

FIG. 4 shows the discharge current Id, excitation current Ia, and a waveform of the output-voltage of the arc-generating circuit 5 in the case where the circuit-closing switch 56 is turned off during a period of time where the spark current Id is below the excitation current Ia. The excitation current also becomes discontinuous in this case and a counter electromotive force occurs in the coil 53, which disturbs the waveform of the discharge current Id. Therefore, the reproducibility of the discharge current is lowered.

In the previous embodiment, the timing of initiating the excitation of the coil 53 is selected so that the excitation current of the coil 53 reaches the target value before the spark discharge is initiated. Alternatively, it is also possible to select the timing of initiating the excitation of the coil 53 so that the excitation current of the coil 53 reaches the target value before the spark current falls below the target value of the excitation current of the coil 53.

After the spark discharge has ceased, it is necessary to recharge the capacitor 13 before the next analysis begins. Therefore, the period of time by which the initiation of excitation of the coil 53 is advanced from the initiation of the spark discharge should be preferably shorter than the charging time of the capacitor 13. This timing scheme prevents the analysis time from being longer even when the excitation of the coil 53 is advanced.

The bypass diode 54 may be replaced by a metal-oxide semiconductor field-effect transistor (MOSFET). In this case, when the arc discharging is not performed, the MOSFET is turned on to reduce conduction loss. When the arc discharge is performed, the MOSFET is turned off to utilize the body diode of the MOSFET as the bypass diode.

It should be noted that the previous embodiment is a mere example of the present invention. It is evident that any change, modification or addition appropriately made within the spirit of the present invention will be included in the scope of the claims of this patent application.

The invention claimed is:

1. An optical emission analyzer comprising:
   an emission stand for generating an excitation emission between a sample and a discharge electrode;
   a capacitor circuit and an igniter circuit, for generating a spark discharge between the sample and the discharge electrode;
   an arc-generating circuit including a power source, a coil and a switching element for exciting the coil by alternately connecting the coil to the power source and disconnecting the coil from the power source, with the igniter circuit, the capacitor circuit and the arc-generating circuit being connected in series to the emission stand to form a discharge path,
   a switching means for changing a state of the arc-generating circuit between a closed state and an open state; and
   a control means for controlling the switching means to coordinate a timing of initiating the spark discharge and a timing of initiating an excitation of the coil so that an excitation current of the coil reaches a predetermined target value before the spark discharge ceases and for controlling the arc-generating circuit so that, after the spark discharge is generated by the igniter circuit, an arc discharge is generated and maintained by the arc-generating circuit.

2. The optical emission analyzer according to claim 1, which is characterized in that the control means initiates the excitation of the coil so that the excitation current of the coil reaches a predetermined target value within a duration of the spark discharge between the sample and the discharge electrode.

3. The optical emission analyzer according to claim 1, which is characterized in that a period of time from the initiation of excitation of the coil to the initiation of the spark discharge is set at a length shorter than a period of time for the capacitor to be charged by the capacitor-charging circuit.

4. The optical emission analyzer according to claim 1, which is characterized in that:
   the switching means includes a circuit-closing switch which is provided in parallel to the emission stand with respect to the arc-generating circuit and closes the arc-generating circuit when it is turned on, and a reverse-blocking diode for preventing a spark current from flowing into the circuit-closing switch; and
   the control means turns on the circuit-closing switch before initiating the spark discharge between the sample and the discharge electrode and turns off the circuit-closing switch after the initiation of the spark discharge during a period of time where the spark current exceeds the excitation current of the coil.

5. The optical emission analyzer according to claim 2, which is characterized in that a period of time from the initiation of excitation of the coil to the initiation of the spark discharge is set at a length shorter than a period of time for the capacitor to be charged by the capacitor-charging circuit.

6. The optical emission analyzer according to claim 2, which is characterized in that:
   the switching means includes a circuit-closing switch which is provided in parallel to the emission stand with respect to the arc-generating circuit and closes the arc-generating circuit when it is turned on, and a reverse-blocking diode for preventing a spark current from flowing into the circuit-closing switch; and
   the control means turns on the circuit-closing switch before initiating the spark discharge between the sample and the discharge electrode and turns off the circuit-closing switch after the initiation of the spark discharge during a period of time where the spark current exceeds the excitation current of the coil.

7. The optical emission analyzer according to claim 3, which is characterized in that:
   the switching means includes a circuit-closing switch which is provided in parallel to the emission stand with respect to the arc-generating circuit and closes the arc-generating circuit when it is turned on, and a reverse-blocking diode for preventing a spark current from flowing into the circuit-closing switch; and
   the control means turns on the circuit-closing switch before initiating the spark discharge between the sample and the discharge electrode and turns off the circuit-closing switch after the initiation of the spark discharge during a period of time where the spark current exceeds the excitation current of the coil.

8. The optical emission analyzer according to claim 5, which is characterized in that:
   the switching means includes a circuit-closing switch which is provided in parallel to the emission stand with respect to the arc-generating circuit and closes the arc-generating circuit when it is turned on, and a reverse-blocking diode for preventing a spark current from flowing into the circuit-closing switch; and
   the control means turns on the circuit-closing switch before initiating the spark discharge between the sample and the discharge electrode and turns off the circuit-closing switch after the initiation of the spark discharge during a period of time where the spark current exceeds the excitation current of the coil.

* * * * *